US009807174B2

(12) United States Patent
Starr et al.

(10) Patent No.: US 9,807,174 B2
(45) Date of Patent: *Oct. 31, 2017

(54) MEDICATION DELIVERY SYSTEM AND METHOD

(71) Applicant: Mylan Inc., Canonsburg, PA (US)

(72) Inventors: Eric W. Starr, Allison Park, PA (US); Dustin D. Updyke, McMurray, PA (US); Sherry M. Korczynski, Bridgeville, PA (US)

(73) Assignee: Mylan Inc., Canonsburg, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/600,572

(22) Filed: May 19, 2017

(65) Prior Publication Data

US 2017/0257436 A1  Sep. 7, 2017

Related U.S. Application Data

(63) Continuation of application No. 14/483,572, filed on Sep. 11, 2014, now Pat. No. 9,692,829, which is a
(Continued)

(51) Int. Cl.
*H04L 29/08* (2006.01)
*H04W 64/00* (2009.01)
(Continued)

(52) U.S. Cl.
CPC .............. *H04L 67/12* (2013.01); *A61M 5/002* (2013.01); *A61M 5/20* (2013.01); *A61M 5/5086* (2013.01);
(Continued)

(58) Field of Classification Search
CPC ...... A61M 5/002; A61M 5/20; A61M 5/5086; A61M 2205/18; A61M 2205/3306;
(Continued)

(56) References Cited

U.S. PATENT DOCUMENTS 4,031,893 A  6/1977  Kaplan et al.
4,394,863 A  7/1983  Bartner
(Continued)

FOREIGN PATENT DOCUMENTS

CN  101770683 A  7/2010
CN  101796533 A  8/2010
(Continued)

OTHER PUBLICATIONS

Google patents search, Feb. 27, 2016, 2 pages.
(Continued)

*Primary Examiner* — Arvin Eskandarnia
*Assistant Examiner* — Gil H. Lee (57) ABSTRACT

A medication delivery system includes a medical server configured to send and receive and process data, a medication device configured to administer a preselected medication, a sensor circuit configured to detect selected parameters relating to medication delivery and transmit information, a transmission hub configured to communicate with the medical server and the sensor circuit. The transmission hub is configured to receive a signal from the sensor circuit and exchange the information. An application is configured to facilitate exchange of information between the sensor circuit and the medical server. The application has a preselected set of protocols. The application monitors usage of the medication device and location of the medication device by connecting to the medication device via the transmission hub.

15 Claims, 4 Drawing Sheets

Related U.S. Application Data continuation-in-part of application No. 13/907,028, filed on May 31, 2013.

(60) Provisional application No. 61/732,753, filed on Dec. 3, 2012.

(51) Int. Cl.
*A61M 5/20* (2006.01)
*A61M 5/50* (2006.01)
*A61M 5/00* (2006.01)
*G06F 19/00* (2011.01)

(52) U.S. Cl.
CPC ...... *G06F 19/3475* (2013.01); *H04W 64/003* (2013.01); *A61M 2205/18* (2013.01); *A61M 2205/3306* (2013.01); *A61M 2205/3368* (2013.01); *A61M 2205/3553* (2013.01); *A61M 2205/3569* (2013.01); *A61M 2205/3584* (2013.01); *A61M 2205/3592* (2013.01); *A61M 2205/52* (2013.01); *A61M 2205/581* (2013.01); *A61M 2205/6054* (2013.01); *A61M 2205/6072* (2013.01)

(58) Field of Classification Search
CPC .. A61M 2205/3368; A61M 2205/3553; A61M 2205/3569; A61M 2205/3584; A61M 2205/3592; A61M 2205/52; A61M 2205/581; A61M 2205/6054; A61M 2205/6072; G06F 19/3475; H04L 67/12; H04W 64/003
See application file for complete search history.

(56) References Cited

U.S. PATENT DOCUMENTS

| | | | |
|---|---|---|---|
| 4,484,910 A | 11/1984 | Sarnoff et al. |
| 4,640,686 A | 2/1987 | Dalling et al. |
| 4,663,621 A | 5/1987 | Field et al. |
| 4,678,461 A | 7/1987 | Mesa |
| 4,695,954 A | 9/1987 | Rose |
| 4,731,765 A | 3/1988 | Cole et al. |
| 4,795,433 A | 1/1989 | Sarnoff |
| 4,832,682 A | 5/1989 | Sarnoff |
| 4,959,358 A | 9/1990 | Carey |
| 5,085,641 A | 2/1992 | Sarnoff et al. |
| 5,092,843 A | 3/1992 | Monroe et al. |
| 5,102,393 A | 4/1992 | Sarnoff et al. |
| 5,221,024 A | 6/1993 | Campbell |
| 5,354,286 A | 10/1994 | Mesa et al. |
| 5,564,803 A | 10/1996 | McDonald |
| 5,710,551 A | 1/1998 | Ridgeway |
| 5,815,586 A | 9/1998 | Dobbins |
| 5,835,455 A | 11/1998 | Hanson et al. |
| 5,914,675 A | 6/1999 | Tognazzini |
| 5,955,947 A | 9/1999 | Sutsos et al. |
| 5,967,975 A | 10/1999 | Ridgeway |
| 6,032,155 A | 2/2000 | de la Huerga |
| 6,109,774 A | 8/2000 | Holmes et al. |
| 6,158,613 A | 12/2000 | Novosel et al. |
| 6,216,925 B1 | 4/2001 | Garon |
| 6,259,356 B1 | 7/2001 | Tamaoki |
| 6,297,737 B1 | 10/2001 | Irvin |
| 6,401,991 B1 | 6/2002 | Eannone et al. |
| 6,471,087 B1 | 10/2002 | Shusterman |
| 6,529,446 B1 | 3/2003 | de la Huerga |
| 6,595,362 B2 | 7/2003 | Penney et al. |
| 6,633,796 B1 | 10/2003 | Pool et al. |
| 6,707,763 B2 | 3/2004 | Osberg et al. |
| 6,825,753 B2 | 11/2004 | Cardinale et al. |
| 6,880,722 B2 | 4/2005 | Anderson et al. |
| 6,937,150 B2 | 8/2005 | Medema et al. |
| 6,941,274 B1 | 9/2005 | Ramachandran et al. |
| 6,958,691 B1 | 10/2005 | Anderson et al. |
| 7,032,752 B2 | 4/2006 | Krackow |
| 7,138,902 B2 | 11/2006 | Menard |
| 7,191,777 B2 | 3/2007 | Brand |
| 7,449,012 B2 | 11/2008 | Young et al. |
| 7,715,277 B2 | 5/2010 | de la Huerga |
| 7,731,686 B2 | 6/2010 | Edwards |
| 7,749,194 B2 | 7/2010 | Edwards et al. |
| 7,819,116 B2 | 10/2010 | Brand |
| 7,941,534 B2 | 5/2011 | de la Huerga |
| 7,996,106 B2 | 8/2011 | Ervin |
| 8,021,344 B2 | 9/2011 | Edwards |
| 8,044,778 B2 | 10/2011 | Monroe |
| 8,048,035 B2 | 11/2011 | Mesa et al. |
| 8,149,111 B2 | 4/2012 | Monroe |
| 8,172,082 B2 | 5/2012 | Edwards et al. |
| 8,206,360 B2 | 6/2012 | Edwards |
| 8,226,610 B2 | 7/2012 | Edwards |
| 8,249,889 B2 | 8/2012 | Lyons |
| 8,272,562 B2 | 9/2012 | Ziegler |
| 8,361,026 B2 | 1/2013 | Edwards |
| 8,487,738 B2 | 7/2013 | Faries et al. |
| 8,505,959 B2 | 8/2013 | Darling, III |
| 8,544,645 B2 | 10/2013 | Edwards et al. |
| 8,593,278 B2 | 11/2013 | Churbock et al. |
| 8,670,865 B2 | 3/2014 | Coe |
| 8,744,620 B2 | 6/2014 | Shavelsky et al. |
| 8,753,308 B2 | 6/2014 | Palmer et al. |
| 8,786,729 B2 | 7/2014 | Peng |
| 8,922,367 B2 | 12/2014 | Denny et al. |
| 9,053,520 B2 | 6/2015 | Vik |
| 2001/0028308 A1 | 10/2001 | de la Huerga |
| 2002/0093429 A1 | 7/2002 | Matsushita et al. |
| 2002/0100472 A1 | 8/2002 | Casper et al. |
| 2002/0173875 A1 | 11/2002 | Wallace |
| 2002/0179622 A1 | 12/2002 | Mase |
| 2002/0188259 A1 | 12/2002 | Hickle |
| 2003/0023146 A1 | 1/2003 | Shusterman |
| 2003/0023345 A1 | 1/2003 | Depeursinge |
| 2003/0090364 A1 | 5/2003 | Cardinale et al. |
| 2003/0174554 A1 | 9/2003 | Dunstone |
| 2004/0099676 A1 | 5/2004 | Anderson et al. |
| 2004/0108795 A1 | 6/2004 | Meek |
| 2004/0158350 A1 | 8/2004 | Ostergaard et al. |
| 2004/0173561 A1 | 9/2004 | Wolfe |
| 2004/0210488 A1* | 10/2004 | Doherty ............ G06F 19/3462 705/22 |
| 2005/0005934 A1 | 1/2005 | Harvey |
| 2005/0023286 A1 | 2/2005 | Pinney |
| 2005/0113969 A1 | 5/2005 | Spano |
| 2005/0146419 A1 | 7/2005 | Porter |
| 2005/0192705 A1 | 9/2005 | Pinney |
| 2005/0258066 A1 | 11/2005 | Conley |
| 2006/0030891 A1 | 2/2006 | Saltzstein et al. |
| 2006/0089545 A1 | 4/2006 | Ratijen et al. |
| 2006/0125356 A1 | 6/2006 | Meek |
| 2006/0139148 A1 | 6/2006 | Faro |
| 2006/0139149 A1 | 6/2006 | Faro |
| 2006/0242295 A1 | 10/2006 | Husemann et al. |
| 2006/0253096 A1 | 11/2006 | Blakley |
| 2006/0267779 A1 | 11/2006 | Ishikawa |
| 2007/0121918 A1* | 5/2007 | Tischer ............ H04M 1/72572 379/373.02 |
| 2007/0125100 A1 | 6/2007 | Schoenfeld et al. |
| 2007/0129708 A1 | 6/2007 | Edwards et al. |
| 2007/0156707 A1 | 7/2007 | Fuchs et al. |
| 2007/0185615 A1 | 8/2007 | Bossi |
| 2007/0186923 A1 | 8/2007 | Poutiatine et al. |
| 2007/0197968 A1 | 8/2007 | Pongpairochana et al. |
| 2007/0204497 A1 | 9/2007 | de la Huerga |
| 2007/0215018 A1 | 9/2007 | Faries |
| 2007/0227204 A1 | 10/2007 | Shoenfeld |
| 2007/0233001 A1 | 10/2007 | Burroughs et al. |
| 2007/0244598 A1 | 10/2007 | Shoenfeld |
| 2007/0272746 A1 | 11/2007 | Ortiz |
| 2007/0285238 A1 | 12/2007 | Batra |
| 2008/0030345 A1 | 2/2008 | Austin |
| 2008/0059228 A1 | 3/2008 | Bossi |
| 2008/0097552 A1 | 4/2008 | Dicks et al. |

(56) References Cited

U.S. PATENT DOCUMENTS

| | | |
|---|---|---|
| 2008/0188813 A1 | 8/2008 | Miller et al. |
| 2008/0202978 A1 | 8/2008 | Saloman et al. |
| 2008/0203107 A1 | 8/2008 | Conley |
| 2008/0249468 A1 | 10/2008 | Edwards et al. |
| 2008/0312715 A1 | 12/2008 | Asirvatham |
| 2009/0030366 A1 | 1/2009 | Hochman |
| 2009/0040874 A1 | 2/2009 | Rooney |
| 2009/0108552 A1 | 4/2009 | Mann, III |
| 2009/0120962 A1 | 5/2009 | Malorni et al. |
| 2009/0128330 A1 | 5/2009 | Monroe |
| 2009/0149894 A1 | 6/2009 | Merry et al. |
| 2009/0164042 A1 | 6/2009 | Handfield |
| 2009/0184022 A1 | 7/2009 | Coe et al. |
| 2009/0187274 A1 | 7/2009 | Higham |
| 2009/0194104 A1* | 8/2009 | Van Sickle ............ A61M 15/00 128/203.12 |
| 2009/0231132 A1 | 9/2009 | Shoenfeld |
| 2009/0294521 A1 | 12/2009 | de la Huerga |
| 2010/0010666 A1 | 1/2010 | Adams |
| 2010/0022953 A1 | 1/2010 | Bochenko et al. |
| 2010/0022987 A1 | 1/2010 | Bochenko et al. |
| 2010/0062748 A1 | 3/2010 | Steinmetz |
| 2010/0160857 A1 | 6/2010 | Pongpairochana et al. |
| 2010/0169111 A1 | 7/2010 | Brue et al. |
| 2010/0204659 A1 | 8/2010 | Bochenko et al. |
| 2010/0211005 A1 | 8/2010 | Edwards et al. |
| 2010/0252036 A1 | 10/2010 | Sutherland et al. |
| 2010/0300130 A1 | 12/2010 | Shoenfeld |
| 2010/0305750 A1 | 12/2010 | Conley |
| 2010/0318035 A1 | 12/2010 | Edwards et al. |
| 2011/0021140 A1* | 1/2011 | Binier .................. H04B 5/0043 455/41.1 |
| 2011/0148624 A1 | 6/2011 | Eaton |
| 2011/0166700 A1 | 7/2011 | Dunn |
| 2011/0231535 A1* | 9/2011 | Starnes ................ H04W 4/001 709/223 |
| 2011/0234419 A1 | 9/2011 | Churbock et al. |
| 2011/0266929 A1 | 11/2011 | Michael |
| 2012/0003928 A1 | 1/2012 | Geboers |
| 2012/0130534 A1 | 5/2012 | Wurm |
| 2012/0182143 A1* | 7/2012 | Gaines ................. A61B 5/0022 340/539.12 |
| 2012/0253837 A1 | 10/2012 | Cashman |
| 2012/0259456 A1 | 10/2012 | Saltsov |
| 2012/0259458 A1 | 10/2012 | Barrett et al. |
| 2012/0274196 A1 | 11/2012 | Arceta et al. |
| 2012/0280815 A1 | 11/2012 | Edwards |
| 2012/0302990 A1 | 11/2012 | De Paula |
| 2012/0310410 A1 | 12/2012 | Adams |
| 2013/0030566 A1 | 1/2013 | Shavelsky et al. |
| 2013/0090594 A1 | 4/2013 | Palmer et al. |
| 2013/0131586 A1 | 5/2013 | Poutiatine et al. |
| 2013/0166066 A1 | 6/2013 | Dunn |
| 2013/0194092 A1* | 8/2013 | Moriarty .............. A61B 5/0022 340/539.12 |
| 2013/0245545 A1 | 9/2013 | Arnold |
| 2013/0262184 A1 | 10/2013 | Jain et al. |
| 2014/0004808 A1 | 1/2014 | Li |
| 2014/0073262 A1* | 3/2014 | Gutierrez ............ H04M 1/7253 455/67.11 |
| 2014/0114277 A1 | 4/2014 | Eggert et al. |
| 2014/0142403 A1 | 5/2014 | Brumback et al. |
| 2014/0155827 A1 | 6/2014 | Ostrander et al. |
| 2014/0218537 A1 | 8/2014 | Nepo |
| 2014/0252927 A1 | 9/2014 | Denny |
| 2014/0357304 A1 | 12/2014 | Ostrander et al. |
| 2014/0379874 A1 | 12/2014 | Starr et al. |
| 2015/0078536 A1 | 3/2015 | Denny et al. |
| 2015/0105903 A1 | 4/2015 | Denny et al. |
| 2015/0250956 A1 | 9/2015 | Ostrander et al. |
| 2015/0251839 A1 | 9/2015 | Denny et al. |

FOREIGN PATENT DOCUMENTS

| | | |
|---|---|---|
| CN | 106797419 A | 5/2017 |
| CN | 107077451 A | 8/2017 |
| EP | 291802 | 3/2003 |
| WO | 96-21925 | 7/1996 |
| WO | 03-043684 | 5/2003 |
| WO | 2005 004961 | 1/2005 |
| WO | 2007-081947 | 7/2007 |

OTHER PUBLICATIONS

International Preliminary Report on Patentability in Related PCT Application PCT-US2015-049232 dated Mar. 23, 2017, 10 pages.
International Preliminary Report on Patentability in Related PCT Application PCT-US2015-044911 dated Feb. 23, 2017, 10 pages.
International Search Report for PCT/US2013/072881 dated Feb. 26, 2014.
International Search Report for PCT/US2013/072878 dated Feb. 26, 2014.
International Search Report and Written Opinion for PCT/US2015/21658 dated Jun. 26, 2015.
International Search Report and Written Opinion for PCT/US2015/44911 dated Jan. 12, 2016.
International Search Report and Written Opinion for PCT/US2015/49232 dated Feb. 1, 2016.

* cited by examiner

MEDICATION DELIVERY SYSTEM AND METHOD

CROSS REFERENCE TO A RELATED APPLICATION

This application is a continuation of U.S. application Ser. No. 14/483,572 filed on Sep. 11, 2015, now allowed, which is a continuation-in-part of U.S. patent application Ser. No. 13/907,028, filed on May 31, 2013, which claims the benefit of U.S. provisional patent application No. 61/732,753, filed on Dec. 3, 2012, the entire disclosures of which are incorporated herein by reference in their entireties.

TECHNICAL FIELD

Various exemplary embodiments disclosed herein relate generally to a configurable medication delivery system, and more particularly to medication delivery system having a smart sensor for remotely detecting and monitoring specific parameters related to the storage and utilization of a medication and/or medication device.

BACKGROUND

Conventional medical systems related to medication delivery are used to monitor medication usage by a patient while the patient is located at a designated health facility. Accordingly, such medical systems monitor or track the amount of drug administered to a patient. This information may be entered into the medical system by the medical practitioner, manually or automatically using devices such as scanners and bar codes. While such systems are suitable for their intended purposes of tracking and monitoring medication usage while the patient and/or medication are both located at the medical facility, most systems do not provide extensive and accurate remote real-time monitoring of medication usage by a user once the user leaves the medical facility. Further most medical systems are incapable of tracking medication received by a user at a pharmacy or by mail.

The foregoing objects and advantages of the invention are illustrative of those that can be achieved by the various exemplary embodiments and are not intended to be exhaustive or limiting of the possible advantages which can be realized. Thus, these and other objects and advantages of the various exemplary embodiments will be apparent from the description herein or can be learned from practicing the various exemplary embodiments, both as embodied herein or as modified in view of any variation that may be apparent to those skilled in the art. Accordingly, the present invention resides in the novel methods, arrangements, combinations, and improvements herein shown and described in various exemplary embodiments.

SUMMARY

A brief summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

Various exemplary embodiments relate to a medication delivery system. The medication delivery system comprises a medical server configured to send, receive and process data, a medication device configured to administer a preselected medication, a sensor circuit configured to detect selected parameters relating to medication delivery and transmit the information, a transmission hub configured to communicate with the medical server and the sensor circuit. The transmission hub is configured to receive a signal from the sensor circuit and exchange the information with the server. The medication delivery system further includes an application configured to facilitate the exchange of information between the sensor circuit and the medical server.

In further various embodiments of the medication delivery system, the transmission hub is a mobile device configured to exchange information with the sensor circuit using Bluetooth™ or Bluetooth Low Energy Technology, and also in communication with the server. The sensor circuit can be attached to the medication device or on a medication carrier.

In further various embodiments, the sensor circuit includes a temperature sensor configured to detect the temperature of the environment surrounding the medication device. The sensor circuit transmits the detected temperature to the transmission hub, and the application compares the detected temperature to a selected temperature range.

In further various embodiments, the sensor circuit includes a location detector configured to provide information regarding the location of the medication device and attached sensor circuit and transmits location related data to the application.

In further various embodiments, the sensor circuit includes a contact element provided on the medication device to facilitate detection of administration of medication from the device by the application. The application may be provided on the transmission hub providing an interface for a user to input information into the application.

Further, various exemplary embodiments relate to a method for remotely monitoring medication delivery at a medication device. The method comprises detecting contact at the medication device using a contact element provided on the medication device, in communication with a sensor circuit. Next, the method step comprises transmitting a signal from the sensor circuit to an application indicating that contact has occurred at the medication device. The method further includes receiving the signal from the sensor circuit at a transmission hub and determining that the signal contains contact element information using the application. The method further comprises sending a signal from the transmission hub to a connected medical server indicating that the medication has been accessed Further, various exemplary embodiments relate to a method for detecting the location of a medication device. The method comprises transmitting a Bluetooth™ signal from a sensor circuit provided on a medication device or on a medication device carrier. The method further comprises receiving the Bluetooth™ signal at a transmission hub, if the signal is within range. The method further comprises initiating a signal from the transmission hub to a remotely connected server providing the location of the transmission hub if the Bluetooth™ signal is received. In the event that the signal is not in range of the transmission hub, the method comprises initiating a signal from the transmission hub to a remotely connected server indicating the sensor circuit is not within range of the transmission hub.

The method further comprises detecting an approximate distance and/or location the transmission hub is from the sensor circuit by sensing the signal strength of the Bluetooth transmission from the sensor circuit. Location the direction of the medication device can be done by displaying the strength of the signal as a user moves closer or away from the device.

The method further comprises detecting the distance or location of the sensor circuit with the medical device by activating a button or signal at the transmission hub or application such that the sensor circuit emits a sound, vibration and a LED. The method further comprises detecting the location of a medication device using a global positioning system application to determine where the transmission hub is located.

BRIEF DESCRIPTION OF THE DRAWINGS

In order to better understand various exemplary embodiments, reference is made to the accompanying drawings, wherein.

To facilitate understanding, identical reference numerals have been used to designate elements having substantially the same or similar structure and/or substantially the same or similar function.

DETAILED DESCRIPTION

For simplicity and illustrative purposes, the principles are shown by way of examples of systems and methods described. In the following description, numerous specific details are set forth in order to provide a thorough understanding of the examples. It will be apparent however, to one of ordinary skill in the art, that the examples may be practiced without limitation to these specific details. In other instances, well known methods and structures are not described in detail so as not to unnecessarily obscure understanding of the examples.

The ability for a medical service provider to monitor and track a patient's medication usage in real-time, assists the medical service provider in providing immediate specialized services to the patient. Real-time tracking or monitoring of a patent's medication usage by the medical service provider may also provide safety advantages to the patient, such as preventing the patient from forgetting to take his/or her medication, preventing the patient from overdosing on a prescribed medication, and providing real-time assistance to the patient during medication administration. Real-time medication tracking further permits the patient or medical service provider to locate misplaced medication, as well as facilitate contacting emergency services or personnel upon usage of the medication.

Electronic devices, such as smart phones or similar transmission hubs, permit a user and/or medical service provider to remotely communicate with a medication device via Bluetooth™, and simultaneously communicate with remote data servers and related networks via the internet, Wi-Fi or cellular. Accordingly, it is desirable to provide a medication delivery system providing a configurable smart sensor circuit and transmission hub in communication with a remote data server, to monitor and track the utilization of a selected medication and/or medication device, and further facilitate the delivering of enhanced specialized medical services to the patient.

Figure 1:
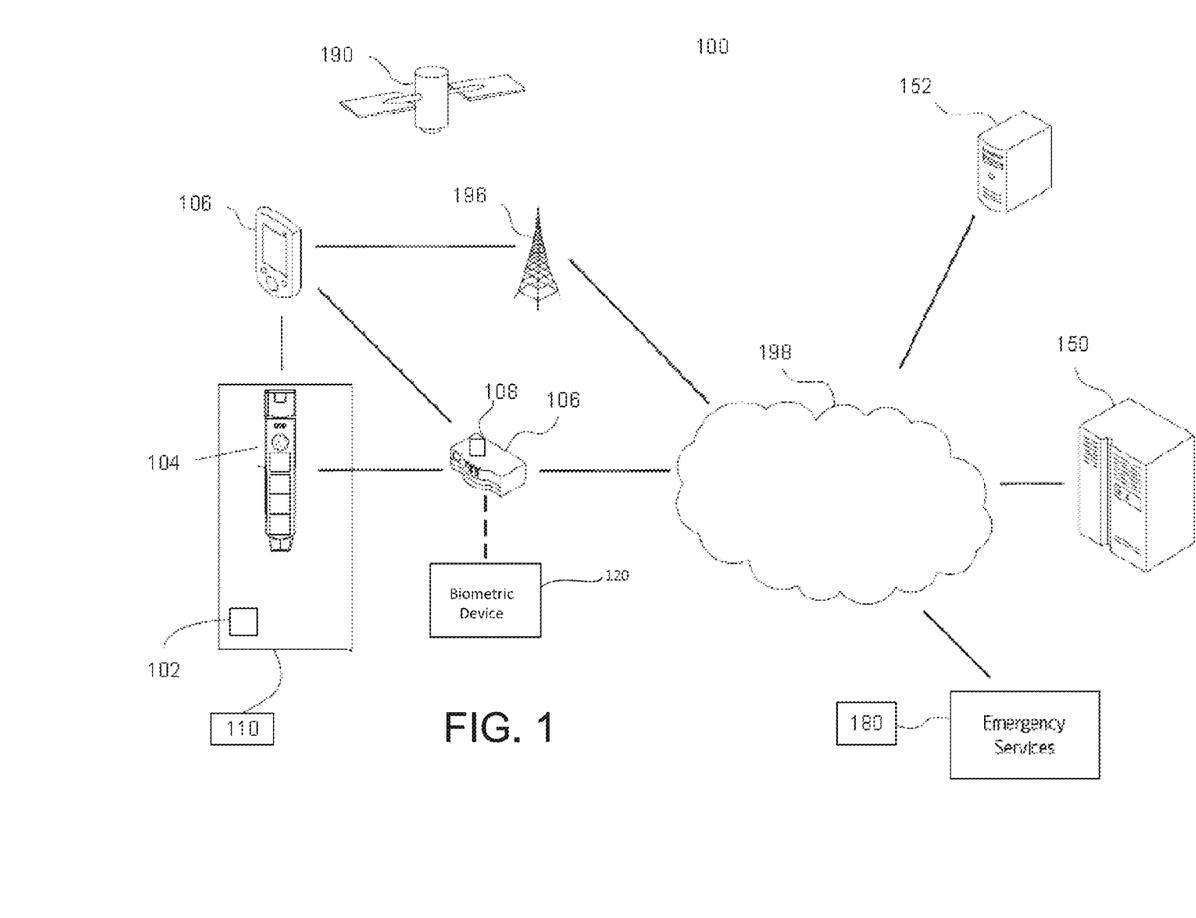
FIG. 1 illustrates an embodiment of a medication delivery system configured to remotely monitor medication usage and location, having a transmission hub in communication with a medication device, and smart sensor circuit.

Referring now to the drawings, wherein the illustrations are for purposes of describing one or more embodiments and not for the purposes of limiting the same, FIG. 1 illustrates an embodiment of the medication delivery system generally designated by the reference numeral 100. The medication delivery system 100, in communication with a smart sensor 102 or smart sensor circuit, facilitates the monitoring and tracking of key parameters associated with a patients usage and storage of a selected medication and/or a medication device 104. Such medical devices may include an auto-injector Epipen®, or an auto-injector Epipen® cap 112, an insulin pen, transdermal patch, metered dose inhaler, dry powder inhaler, Nebulizer, Glatitramer Acetate Pen, for example. Notably, it is contemplated that the smart sensor 102 may operate in conjunction with any medical device used to distribute mediation, without departing from the scope of the invention.

The medication delivery system 100 includes a smart sensor circuit 102. The smart sensor 102 may be configured to detect and facilitate the exchange of medication-specific information to and from the medication device 104, to a remote medical server 150 and associated networks. The smart sensor 102 may be provided on the medication device 104, in the cap portion 112 of the medication device 104, or on an associated medication carrier 110, which may be a package, or container.

As indicated, the medication delivery system 100 generally includes a medical server 150, and further includes a transmission hub 106, in remote communication with the smart sensor 102 and medical server 150. The transmission hub 106 facilitates the transmission and exchange of medication-specific information detected by the smart sensor 102, between the remote medical server 150 and smart sensor circuit 102. The medication delivery system 100 further includes a software application 108. The application 108 operates in cooperation with the medication delivery system 100 platform, and is configured to perform various functions related to collecting, storing, monitoring and remotely transferring medication-specific information between the user and/or medical provider, the transmission hub 106 and the medical server 150.

The medication delivery system 100 may further include one or more biometric devices 120, for measuring patient-specific health related data and transmitting that information to the transmission hub 106 and/or application 108. It is contemplated that the biometric device 120 is configured to transmit this information via wireless and/or Bluetooth.

The smart sensor circuit 102 may include one or more various types of sensors for detecting pre-selected parameters provided by the application 108. The smart sensor 102 may include a physical location sensor 122 configured for detecting conditions related to the physical location of the medication device 104. The physical location sensor may incorporate features such as Global Positioning Systems GPS 190 to provide location specific information as to where the medication device 104 is located. This feature may be advantageous in circumstances that the medication is misplaced, or a medical service provider needs to locate the patient with the medication.

The smart sensor circuit 102 may be an integrated circuit, including additional sensors for detecting parameters such as temperature with a temperature sensor 124, pressure via a pressure sensor 126, mass air flow via a sensor 128, magnetic field (Hall Effect) electrical conductivity detector 130, electrical impedance with a sensor 132, strain and sound via sound detector 134, colorimetric sensor 136 for detecting the color of the medication, among many other parameters.

The temperature sensor 124, provided with the sensor circuit 102, may be configured to continuously measure the real-time temperature of the medication and/or the storage location of the medication. As the temperature sensor 124 provides temperature readings via the sensor circuit 102 to the application 108, the information may be relayed to, and processed by the medical server 150. Such temperature information may be compared to approved storage temperatures for the medication by the application 108 and/or server, and alerts may be sent to the patient via the transmission hub 106, when the medication is located in undesirable conditions. As such, the application 108 in communication with the temperature sensor 124 and sensor circuit 102 can further measure the time frame in which the medication device 104 and medication are located in unapproved temperatures, indicating possible medication degradation.

For example, with respect to a medication such as Epinephrine, the approved temperature range is approximately 15-30 degrees C. As such, in circumstances that the temperature sensor 124 detects that the temperature of the medication is reading is outside of a pre-selected approved range, an indicator 170 prompted by the application 108, may sound an alarm, alert, or message via an interface provided on the transmission hub 106, or external device provided on the medication device 104 or carrier 110.

The smart sensor circuit 102 may further include a microcontroller 142, which may be a small computer including a processor core 144, memory 146, and programmable input/output peripherals 148. For detection of parameters that require an analog sensor it is contemplated that the smart sensor circuit 102 may include an analog to digital converter 140 ("ADC") for converting signals received from the analog sensor to digital signal, such as a Texas Instruments 8/16/32 bit MCU, for example. The memory 146 may be provided on the microcontroller 142. Memory 146 may be provided in the form of a NOR flash or OTP ROM, as well as a RAM. Further, the microcontroller 142 may be configured to receive embedded applications, such that the medication monitoring application 108 may be stored on the smart sensor circuit 102.

The smart sensor circuit 102 may further include, or be in communication with, a transmitter 116 such as a Bluetooth™ Low Energy Radio ("BTLE"), or infrared transmitter, for example, for transmitting data and/or information detected by the smart sensor circuit 102 and the other aforementioned sensors to the transmission hub 106. It is contemplated that in place of a ("Bluetooth™ Low Energy") BTLE Radio transmitter 116 and microcontroller 142, a module 118 which incorporates all functionality of a BTLE radio 116 and microcontroller 122 with an ADC 140, may be provided. The microcontroller 122 may one similar to that manufactured by Microchip, for example. It is further contemplated that the sensor circuit 102 may incorporate other forms of communication such as, RFID, NFC, or other forms of wireless communications to communicate with the transmission hub 106, or directly with the medical server 150. Each sensor circuit 102 may have a unique radio number, which may be transmitted to the transmission hub 106 and application 108 during communication. This unique identifier may permit the application 108 and user to track multiple medication devices 104 simultaneously, and further permit the transmission hub 106 and circuit 102 to be automatically paired.

The location of the sensor circuit 102 and medical device 104 can be determined using intuitive guidance by sensing the signal strength of the Bluetooth transmission. Location the direction of the medication device 104 may be achieved by displaying the strength of the signal, at the transmission hub 106, as a user moves closer or away from the medication device 104. It is also contemplated that the detection of the distance, and/or location of the sensor circuit 102 on medical device 104, can be accomplished by activating a button or signal at the transmission hub 106 or application 108 such that the sensor circuit 102 emits a sound, vibration and a LED, such that the user can detect the location of the sensor circuit 102. Further, it is contemplated that if the transmission hub 106 or sensor circuit 102 and medication device 104, is moving out of range, or pairing is disconnected, the application 108 in cooperation with the transmission hub 106 may generate a notification to the user indicating that the sensor circuit 102 and device 104 is no longer in pairing range. The last detected location of the device 104 may be sent to the application 108 and server 150.

It is contemplated that a transmission hub 106 in range of the sensor circuit 102 may in real-time automatically upload location information to the application 108 and server 150. It is further contemplated that whenever a user activates a "locate" command using the application, the server 150 and/or application 108 will provide the medication devices 104 last detected location. As such, the application 108 can use GPS and/or the signal strength of Bluetooth to indicate the location of the medication device 104. Further, upon reaching the location of the device 104, as previously discussed, the sensor circuit 102 emits a sound, vibration and a LED, such that the user can detect the location of the sensor circuit 102.

The medication device 104 may include one or more medications and/or drug delivery products for treating emergency and/or other medical conditions, such as for example Epinephrine (EpiPen® Auto-Injector), Glatiramer acetate (Copaxone® auto-injector), Adalimumab (Humira® auto injector), Insulin (auto-injector), Naxolone (auto injector) and various respiratory medication delivery devices (metered dose & dry powder inhalers). In various exemplary embodiments, the medication device 104 may be an auto-injector for administering a dose of epinephrine, metered dose & dry powder inhalers or other devices. Suitable auto-injectors and associated devices and method are described by U.S. Pat. Nos. 4,031,893; 4,226,235; 4,329,988; 4,394,863; 4,484,910; 4,640,686; 4,678,461; 4,795,433; 4,832,682; 5,085,641; 5,092,843; 5,102,393; 5,295,965; 5,354,286; 7,449,012; 7,794,432; and 8,048,035, all of which are hereby incorporated by reference in their entireties for all purposes.

Figure 2:
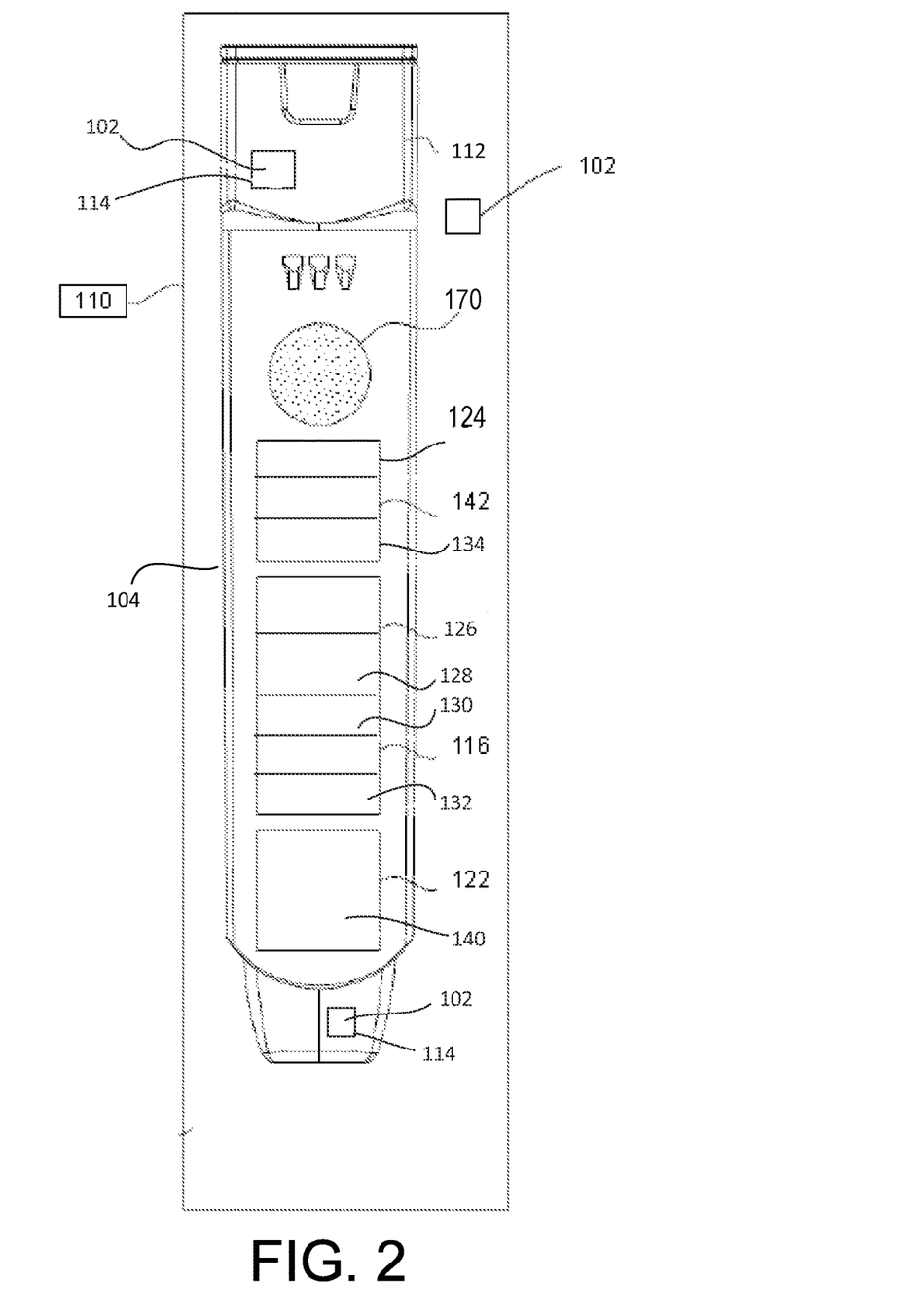
FIG. 2 is a perspective view of an exemplary medication device including a smart sensor circuit provided on the case, to facilitate monitoring of the location and usage of the medication device.

The smart sensor circuit 102 is configured to detect medication-delivery related parameters, specified by the application 108, such as when the medication device 104 is being utilized or activated. Accordingly the smart sensor 102 may further include a contact or frangible element 114. The contact element 114 is configured to detect and generate a signal or indication when a surface is contacted, opened or closed. The contact element 114 may complete or break an electronic circuit when the medication device 104 is activated or packaging 110 is opened, sending a signal to the smart sensor circuit 102.

For example, the smart sensor circuit 102 in cooperation with the contact element 114 is configured to detect when an auto-injector packaging lid 110 is opened, and therefore when an injection of medication, such as epinephrine, insulin, naloxone or another drug, is about to be deployed, further indicating when an injection is underway by a user. Additionally, the smart sensor circuit 102 in cooperation with a contact element 114 provided on the medication device 104 is configured to detect when a needle of an Epipen® is retracted or capped, and the injection is complete. Such detection may be facilitated using one or more contact elements 114. The use of sensors 102 and contact elements 114 are operable with respect to other medication device 104 embodiments. With respect to alternative medication delivery devices 104, such as a dry powder inhaler, for example, the smart sensor circuit 102 may be configured to detect various events with respect to delivery. In the case of a medication device 104, such as an inhaler 104, for example, the sensor circuit 102 in cooperation with the element 114 detects when a lid of the medication device 104 is removed from a dry powder inhaler, metered dose inhaler, nebulizer.

Further the smart sensor circuit 102 may detect when the medication delivery device 104 is grasped by a person. Further, in cooperation with a pressure sensor 126, the sensor circuit 102 may detect when pressure is increased inside or around an inhalation or nasal spray device 104 or when force is applied to a pressurized device. In such cases, generally pressure is needed in order to disperse medication from the medication device 104, such as a metered dose medication canister, thus the sensor circuit 102 detection of force applied to the pressurized device indicates that the medication is in the process of being delivered. This information can then be transmitted remotely to the application 108 and medical server 150

With respect to a medication delivery device 104, such as transdermal delivery patch, for example, the sensor circuit 102 in cooperation with the contact element 114, is configured to detect when the packaging of a transdermal delivery patch 104 is opened, as well as, when the patch is placed on the skin indicating that medication is being delivered.

The medication device 104 may be provided in a carrier 110 or packaging, which may be imprinted with a variety of selected medication information. Such medication information may also be provided on the sensor circuit 102, medication application 108, or remotely stored in a medical server 150. For example, medication information may include the name of the medication, active ingredients, dosage, expiration date, lot ID, approved storage temperature and product serialization number, as well as other medication-specific related information. The medication information may be printed in a manner that is machine-readable. For example, the medicament information may be printed as a quick response (QR) code. The medication information may also be printed as text that is easily recognized using optical character recognition (OCR). As an alternative to storing all of this medication information within one of these codes, the code can be transmitted to a look-up table stored within the application 108, or within the server 150. The code can be used to remotely look-up the information assigned to the particular code. Code assignment can be done at the time of manufacturing or packaging by the manufacturer. Because this information may be stored remotely, the medication information can also be accessed or modified.

The carrier 110 may also include inserts or cards included therein. Any information included on the medication device 104 may instead be located on packaging 110. As will be discussed in further detail below, the medication information may also be digitally encoded in the memory 146 of the medication device 104 or smart sensor 102, permitting the information to be shared with the medication application 108 and the medical server 150.

The transmission hub 106 may be configured to facilitate communication between the smart sensor circuit 102, medication application 108 and the remote medical server 150. The transmission hub 106 transmits information detected by the smart circuit 102 and transmits the information to the medical server 150 or processor. The transmission hub 106 may include a Smart Phone, such as an IPhone™, for example, a Personal Digital Assistant ("PDA"), a computer, tablet, such as an Ipad™, for example, or a hub, such as a Bluetooth™ hub capable of transmitting information remotely such as a 2net Hub manufactured by Qualcomm, Inc- Multiple transmission hubs 106, or electronic devices may be used to track each medication device 104 along with its sensor circuit 102. This may be accomplished using a unique digital code that the manufacturers of radios (Bluetooth, Bluetooth Low Energy, RFID, NFC, etc.) assign to each specific radio chip or sensor circuit 102 during the manufacturing process. Accordingly, the unique digital code assigned to each corresponding radio/chip or sensor 102 can also be assigned to the drug or medication device 104, providing each respective medication device 104 with a separate identity.

Identifying the medication device 104 may be accomplished using the transmission hub 106 that has the application 108 installed on the hub 106, or remotely on the server 150. Accordingly, device identification can be achieved using multiple transmission hubs 106 (phones, tablets, electronic devices) since the code may be assigned to and transmitted from the device sensor 102.

The medication application 108 is configurable to receive, process and transfer information related to the delivery of one or more selected medications. The application 108 may be stored or provided in the medical delivery system's architecture, on either/or the transmission hub 106, the sensor circuit 102 or remotely on the medical server 150 or connected networks. The medication application 108 is configured to monitor a variety of parameters, and/or attributes related to the delivery of medication. The application 108 provided on the transmission hub 106, such as a mobile phone, may provide pre-selected information in real-time to the user/patient, as well as any other authorized individuals accessing the mobile device 106.

The application 108 in communication with the sensor circuit 102 is configured to detect the physical location of the medication device 104, such as an EpiPen®, and provide status alerts and other information when the device 104 is in a range of the transmission hub 106, and additionally when the device is out of range of the transmission hub 106. As such, the system 100 can detect the proximity the device 104 is to a patient, such as a child, and relay this information to a doctor or parent.

The application 108 is also in communication with one or more biometric devices 120. The biometric device 120 provides patient-specific data detected and/or collected when the user uses the biometric device 120. This information is transmitted to the transmission hub 106 in real-time and further transmitted to the application 108 and medical server 150. As such, a medical professional such as a doctor or nurse can monitor the patient's biometric data remotely and adjust medication dosage and prescriptions based on the biometric information. Further a medical provider may remotely program dosage release.

The application 108 is further configured to provide a variety of configurable user settings, such as detection of medication of utilization. The application 108 is further configured to receive a signal from the sensor circuit 102 detecting when the packaging 110 lid is opened, and thus an injection of the medication (e.g. epinephrine, insulin, naloxone or another drug) is about to commence. The application 108 is configured to process and exchange this information with the medical server 150. The application 108 may be configured to monitor other events such as when an auto injector lid is opened, when an auto-injector needle is deployed and retracted, and/or when the injection is completed. Such delivery-specific information may be stored by the application 108, as well as transmitted to the medical server 150. With respect to the other aforementioned medication devices, the application 108 is configured to monitor and transmit usage information remotely to the medication server 150.

As the medication usage event may be stored by the application 108 and/or transmitted to the server 150, such processed usage data may be provided in real-time to the mobile device, or transmission hub 106. The application 108 may provide, for example a map to a medical provider or user, indicating when and where the user has administered the medication device 104 in the past. Additionally, the application 108 could also present a real-time alert as to when the medication 104 has been used, including location information. The application 108 may also provide historical data and analysis of the medication device 104 usage events such as event listings and graphs.

The application 108 is configured to exchange information with the remote medical server 150. The application 108 provides one or more prompts or inputs, permitting the user or medical provider to provide selected information, such as demographic information, geographic information, as well as user activities such as for example, exercise and meal entries. The application 108 may further interface with other medical devices to exchange user medical and biometric information, such as, for example, a blood pressure monitor, a glucometer, pulse oximeter, a weight scale, EKG, and any other medical device configured to transfer medical related information.

The medication delivery system 100 may include a cloud computing infrastructure capable of receiving a signal from the smart sensor circuit and/or application 108 and remotely transmitting information to a processor or cloud computer server 150. The transmission hub 106 is in communication with the server or group of servers, which may be connected via a communication network 198 such as the Internet, an intranet, a local area network (LAN), wide area network (WAN), cellular 196, Wi-Fi, for example. The connected transmission hub 106 or application 108 provided on the transmission hub 106 or server 150 includes preselected permissions and protocols permitting communication and remote access to the medical server 150 by the transmission hub 106.

Medical server 150 may be a server operated by a health care provider, health insurance provider, or government health agency. In addition to storing medication-specific information, the medical server 150 may store, or have access to, patient-specific information. Accordingly, the medical server 150, in communication with the transmission hub 106 may provide patient-specific information to authorized devices, such as the transmission hub 106, an associated medication device control center 180, as well as emergency services providers 180.

As the medical server 150 may be configured to receive and process particular messages from the medication device 104, mobile device or transmission hub 106, and control center 180. For example, medical server 150 may be configured to verify medications, prescriptions and order refills. The medical server 150 may include a processor 160 and/or controller which may me any suitable type of computer processor, such as a microprocessor, configured to perform calculations, determinations, data transmission or data reception, sending or receiving of control signals or commands processed. As used herein, the term "processor" will be understood to encompass a variety of devices such as, for example, microprocessors, field-programmable gate arrays (FPGAs), application-specific integrated circuits (ASICs), and other similar processing and computing devices.

The medical server 150 has the processing power to run an application 108, store data, or perform any other computing task permitting a user to access and run application 108 remotely as the medical server 150 as previously stated, is also connected to a network via the Internet or other connection platforms to be accessed from anywhere.

Medical server 150 may be operated by a medicament manufacturer or other third party. It is contemplated that the medical server 150 may provide the application 108 in a downloadable a format for execution on the transmission hub 106 or may store application on the memory 152 or remotely. The medical server 150 may also provide support for the downloadable application and/or a web application. The medical server 150 may include a database of registered medicament information provided by patients who opt to register the medicament device 104. The medical server 150 may provide various services accessible via the application. The medication server 150 in cooperation with the medication application 108, may provide textual, or audio and/or video instructions that may be downloaded or streamed to the transmission hub or mobile device 106.

The medical server 150 may provide information to the application 108 and transmission hub 106 based on registration medication device 104 information. For example, the medical server 150 may track expiration dates, medication device usage 104 and provide notification of approaching expiration dates. As such, the system 100 can cue reorders when a medication is set to run out or expire in the device 104. In various embodiments, the medical server 150 may provide a tracking system, such as a geo-location tracking system, permitting a registered user to track the last known physical location of the medication device 104 or transmission hub 106 in communication with the device 104.

The medication system 100 in conjunction with the medication server 150 may further include a storage device or memory 152 in communication with the medical server 150 to store data and information. The memory may be provided on the medical server 150 or be externally accessible by the medical server 150. The memory 152 can be any suitable type of computer readable and programmable memory. Examples of computer readable media include a magnetic recording apparatus, non-transitory computer readable storage memory, an optical disk, a magneto-optical disk, and/or a semiconductor memory (for example, RAM, ROM, etc.). Examples of magnetic recording apparatus that may be used in addition to memory 152, or in place of memory 152, include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW.

Memory 152 may store information regarding the medication device 104. Information stored by memory 152 may include the manufacture date, expiration date, medication, dose size, audio instructions, text instructions, other instructions, prescription information, re-order information, and contact information.

The sensor circuit 102 provided on the carrier 110 permits a medical provider to track the carrier for the purposes of reordering and/or recycling the carrier 110. As usage of the carrier 110 is completed, the sensor circuit 102 provided on the carrier 110 may transmit location information to the system 100 via the transmission hub 106. To reduce cost and waste, the sensor circuit 102 may be tracked to a return location via a transmission hub provided at a medical provider's location. As such, the medical provider may detect the sensor circuit 102 once the carrier 110 is range, prompting the medical provider to reorder a replacement medication device 104 for the user.

In operation, the drug delivery system 100 in cooperation with the sensor circuit 102, transmission hub 106, application 108 and a remote medical server 150 provide real-time monitoring of the medication device 104, which may include the temperature of the medication, the approximate location of the medication via location detection of the transmission hub 106, and further medication is administration and usage information.

Figure 3:
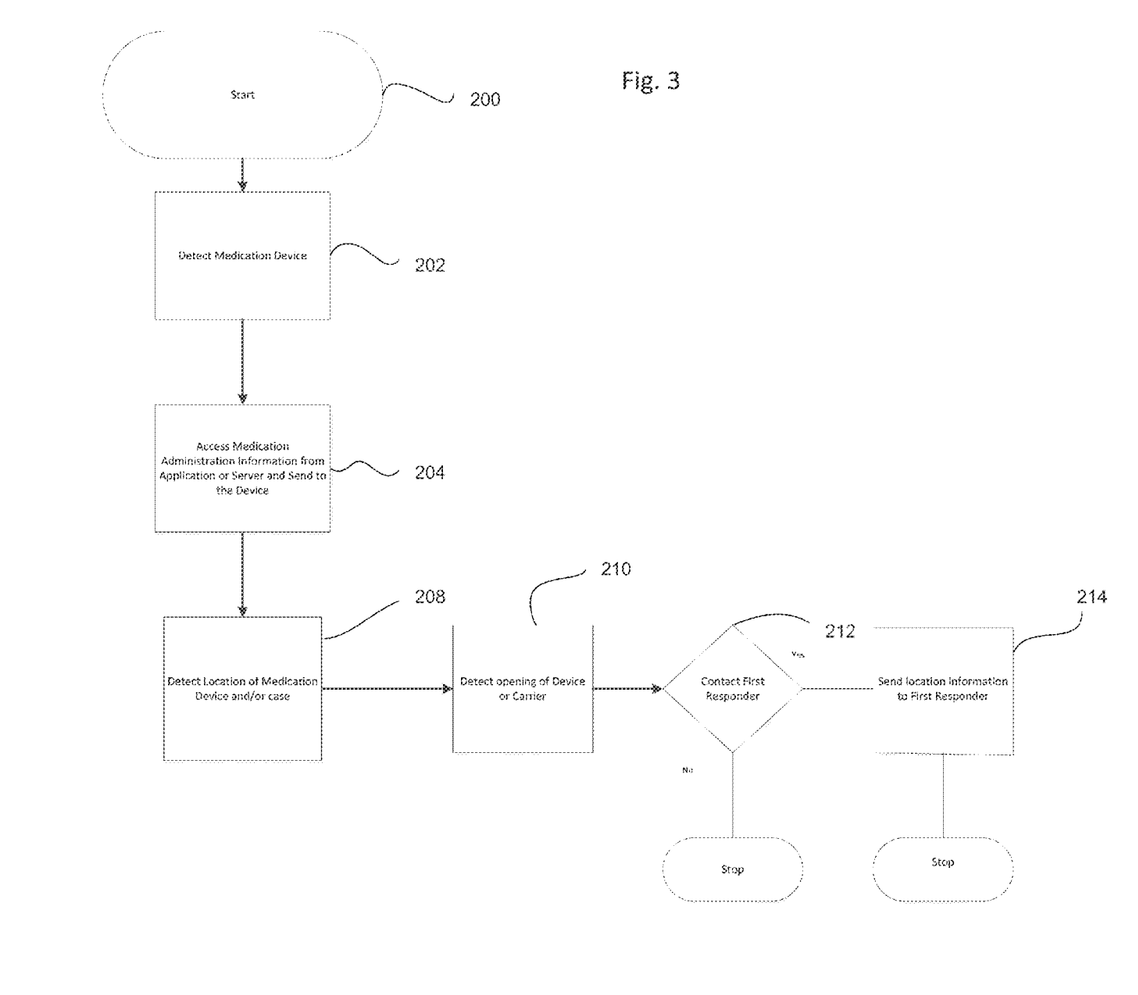
FIG. 3 is a flow diagram illustrating an embodiment of the method of monitoring the location of the medication device in the medication delivery system of FIG. 1.

As previously disclosed, the sensor circuit 102 is connected or affixed to the medication device 104, which may include connection to an EpiPen® cap 112, an auto injector plastic case 110 or carrier 110. As shown in FIG. 3, in step 202 the sensor circuit 102, using a contact element 114 detects when the auto-injector packaging lid is opened and drug usage is about to commence. The sensor circuit 102 may also further detect when the auto-injection needle is deployed and when the injection is commencing and further, when the needle is retracted.

In step 204 and 206, once medication delivery is detected by the smart sensor circuit 102, the application 108 may access administration information via the application 108 and deliver that information containing a series of audios, video or text prompts to be sent to the transmission hub 106 or mobile device 106 in a pre-selected order. The administration information may be transmitted in accordance with a related protocol instructing the patient or user on how to use the medication device 104 properly and how to deliver the medication. The system 100 further detects the location 208 of the transmission hub 106.

Additionally, in step 210 when the auto-injector or medication device 104 is detected by the sensor circuit 102 as being opened, and/or detects that the medication device 104 is deployed, the sensor circuit 102 may send a signal at step 212 to the application 108 prompting the user to determine if they want to the transmission hub 106 or connected server 150, or associated network devices, to contact a first responder, caregiver, medical professional or an emergency number, such as 911.

Information regarding the medication device 104 and carrier 110, and location may be sent to the server 150 via the application 108. This which may be done automatically once medication device 104 is in range of a transmission hub 106 or manually into the application 108 at the transmission hub 106. The medication delivery system 100 in real-time continuously detects when the sensor circuit 102 provided proximate to the medication device 104 is in communication with the transmission hub 106, sending a signal detecting whether the sensor 102 is within range of the transmission hub 106. Medication device 104 detection generally depends on the range of transmission between the sensor circuit 102 and the transmission hub 106, which in the case of Bluetooth™, is approximately 150 ft. It is contemplated that the medication device 104 may also be tracked using GPS chip or cellular communication with the sensor circuit 102. Application 108 or transmission hub 106 may convert the device 104 detected GPS coordinates to text message or audible speech command. As such, once the emergency provider receives the call, an audible speech command will alert the provider of the need for medical attention and the detected location of the medication device 104 and user.

Figure 4:
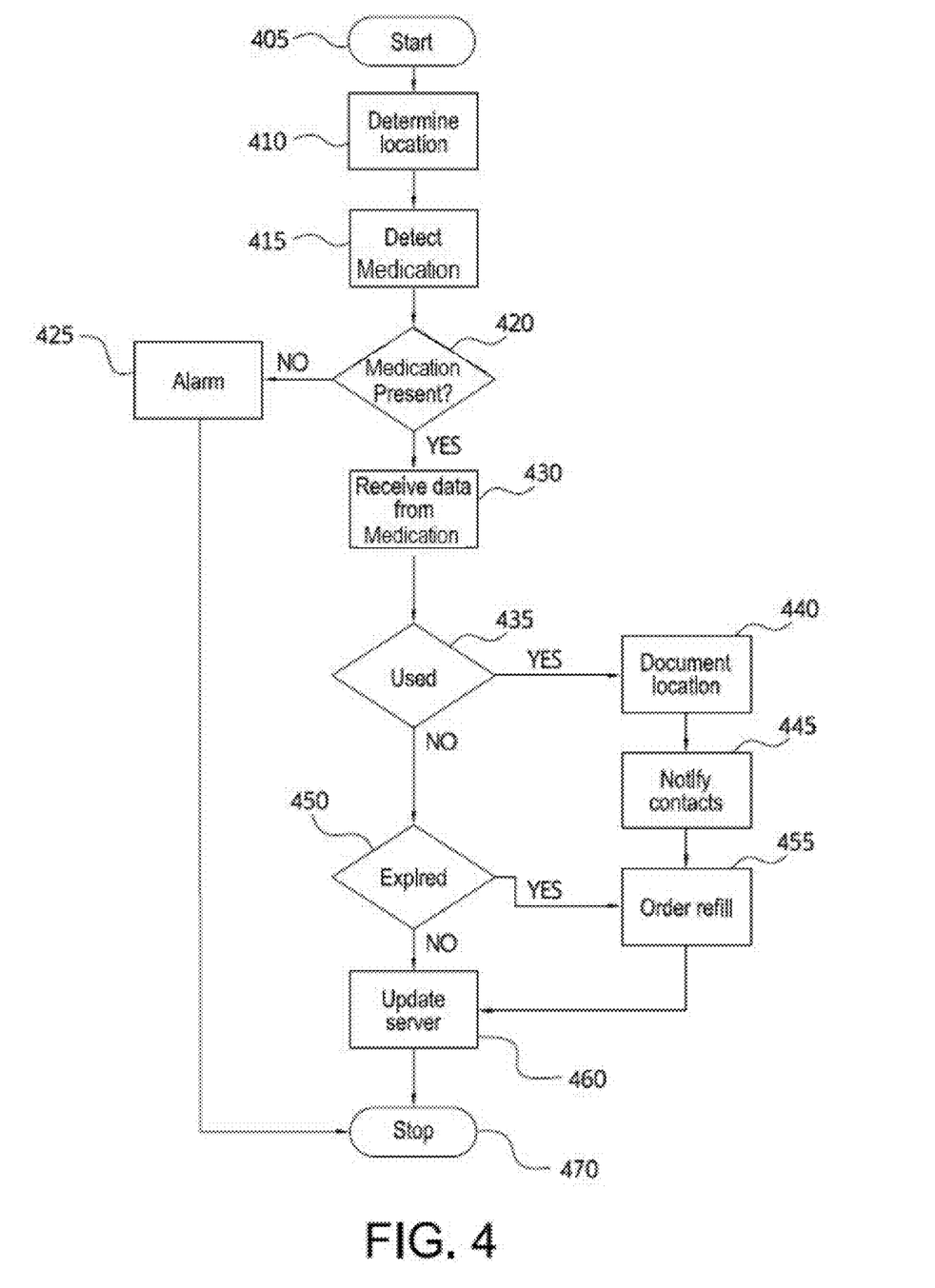
FIG. 4 is a flow diagram illustrating an embodiment of the method of detecting medication usage.

As discussed the application 108 may detect the location of the medication device 106. When the BTLE signal is present, the application 108 may deduce that the medication device 104 is within proximity of the transmission hub 106 and therefore the patient has their medication nearby. This information can be sent to the cloud/medical server 150 and then relayed to caregivers (such as parents) that the patient has their medication on hand. When the BTLE signal is lost, deducing that the medication is most likely not nearby, the application 108 can send an alert to the patient or caregiver FIG. 4 illustrates monitoring usage of the medication device 104. In steps 405 and 410, multiple location signals may be exchanged between the transmission hub 106, sensor circuit 102 and application 108 to provide real-time information with respect to the medication devices 104 and carrier's 110 proximate location. In step 420 and 425, if the sensor circuit 102 leaves the range of detection by the transmission hub 106, a message is sent to the user notifying the user. Further if the sensor returns to range or is reactivated in range of the transmission hub 106, a message is sent to the user.

Using location information and usage information, the system 100 in conjunction with the application 108 may utilize the transmission hub 106 or mobile devices location tracking service to locate the patient and in step 435, send a message to 911 and/or to a caregiver step 445 any time that an emergency medication such as naloxone, epinephrine or corticosteroid is delivered and a refill may be ordered at step 455. The user can also configure additional contact preferences when a medication delivery event occurs.

The system 100 may further provide assistance with respect to monitoring storage and usage and ordering. It is contemplated that once the medication device 104 is opened, the application 108 prompts the user to provide information as to whether they used the medication, and whether they would like to place a reorder for replacement/refill of medication The patient's medication utilization can also be sent to the medical server 150 via the sensor circuit 102 and transmission hub 106 with a time-stamp in order to longitudinally plot medication adherence for maintenance drugs such as insulin, Copaxone®, or a bronchodilator Combining medication delivery times and doses, measured or keyed-in, with biometrics measured by the associated biometric device 120 permits medical personnel that is managing the patient remotely to view effects and side effects such as changes in heart rate, respiration, blood pressure, oxygen saturation and/or body temperature from the patient's. The connected biometric device 120 further permits a medical provider to compare variables such as dosage, diet and exercise to the patient's biometric changes.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be effected while remaining within the spirit and scope of the invention. Accordingly, the foregoing disclosure, description, and figures are for illustrative purposes only and do not in any way limit the invention, which is defined only by the claims.

What is claimed is:

1. A medication delivery system, comprising:
a medication device configured to administer a preselected medication;
a sensor circuit associated with the medication device and configured to detect selected parameters relating to medication delivery with the medication device; and
a transmission hub configured to:
communicate with the sensor circuit and receive a first signal from the sensor circuit;
cause the sensor circuit to emit a first type of alert based on a signal strength value of the first signal between the transmission hub and the sensor circuit being greater than a first preselected value indicative of a first distance between the transmission hub and the sensor circuit, wherein the first type of alert comprises at least a first audible sound;
cause the sensor circuit to emit a second type of alert based on the signal strength value of the first signal between the transmission hub and the sensor circuit being greater than a second preselected value indicative of a second distance between the transmission hub and the sensor circuit, wherein the second distance is greater than the first distance, and wherein the second type of alert comprises at least a second audible sound varying at least one characteristic of the first audible sound; and
transmit a second signal if the signal strength value is less than the first preselected value.

2. The medication delivery system of claim 1, further including at least one biometric device in communication with the transmission hub to transmit patient-specific biometric information to the transmission hub.

3. The medication delivery system of claim 1, wherein the transmission hub is a mobile device configured to exchange information with the sensor circuit using Bluetooth technology.

4. The medication delivery system of claim 1, wherein the sensor circuit is provided on a medication carrier.

5. The medication delivery system of claim 1, wherein the sensor circuit is attached to the medication device.

6. The medication delivery system of claim 5, wherein the sensor circuit includes a temperature sensor configured to detect the temperature of an environment surrounding the medication device such that the sensor circuit transmits the detected temperature to the transmission hub.

7. The medication delivery system of claim 5, wherein the sensor circuit includes a location detector configured to provide information regarding the location of the medication device and attached sensor circuit.

8. The medication delivery system of claim 5, wherein the sensor circuit includes a contact element provided on the medication device to facilitate detection of administration of medication from the medication device.

9. The medication delivery system of claim 1, wherein the transmission hub is a tablet.

10. The medication delivery system of claim 1, further comprising:
a medical server in communication with the sensor circuit and configured to send, receive, and process data; and
an application configured to facilitate exchange of information between the sensor circuit and the medical server, the application having a preselected set of protocols.

11. A method for remotely monitoring medication delivery at a medication device, comprising:
detecting contact at the medication device using an element provided on the medication device, in communication with a sensor circuit;
transmitting, by the sensor circuit, a contact signal from the sensor circuit to an application indicating that contact has occurred at the medication device;
receiving the contact signal from the sensor circuit at a transmission hub;
determining, by the application, that the contact signal contains contact element information;
sending, by the transmission hub, an access signal from the transmission hub to a connected medical server, the access signal indicating that the medication has been accessed;
accessing, by the application, administration information and delivering the administration information in a pre-selected order to at least one of the transmission hub or a mobile device associated with the medication device; and
detecting, by the transmission hub, a location of the medication device by:
detecting a signal strength of the contact signal between the sensor circuit and the transmission hub and comparing the signal strength value to a first preselected value;
causing, by the transmission hub, the sensor circuit to emit a first type of alert comprising a first audible sound based on the signal strength value of the contact signal between the transmission hub and the sensor circuit being greater than the first preselected value indicative of a first distance between the transmission hub and the sensor circuit; and
causing, by the transmission hub, the sensor circuit to emit a second type of alert comprising a second audible sound varying at least one characteristic of the first audible sound based on the signal strength value of the contact signal between the transmission hub and the sensor circuit being greater than a second preselected value indicative of a second distance between the transmission hub and the sensor circuit, wherein the second distance is greater than the first distance.

12. The method of claim 11, further comprising:
transmitting, by the sensor circuit, a prompting signal from the sensor circuit to the application responsive to the application determining that the contact signal contains contact element information;
receiving the prompting signal at the application;
prompting, by the application, a user for an emergency provider in response to receiving the prompting signal; and
contacting the emergency provider by at least one of the transmission hub or the medical server.

13. The method of claim 11, wherein detecting the location of the medication device includes using a global positioning system application to determine where the transmission hub is located.

14. The method of claim 11, wherein the transmission hub is a mobile device configured to exchange information with the sensor circuit using Bluetooth technology.

15. The method of claim 11, wherein detecting contact at the medication device further includes using at least one of a contact element provided on the medication device, a magnetic field sensor, or a force pressure element provided on the medication device.

* * * * *